United States Patent [19]
Essig et al.

[11] Patent Number: 5,709,679
[45] Date of Patent: Jan. 20, 1998

[54] MYOMA REMOVAL TECHNIQUE AND ASSOCIATED SURGICAL DEVICE

[76] Inventors: Mitchell N. Essig, 227 High Brook Ct., Pelham, N.Y. 10803; Peter J. Wilk, 185 West End Ave., New York, N.Y. 10023

[21] Appl. No.: 205,580

[22] Filed: Mar. 3, 1994

[51] Int. Cl.$^6$ ............................................. A61N 5/00
[52] U.S. Cl. ............... 606/46; 606/37; 606/41; 606/45; 607/101; 607/156; 128/898
[58] Field of Search ................ 606/32, 33, 39, 606/45, 50, 46, 34, 41, 198, 192; 604/96; 128/899

[56] References Cited

U.S. PATENT DOCUMENTS

| | | |
|---|---|---|
| 1,919,543 | 7/1933 | Doane . |
| 4,060,087 | 11/1977 | Hiltebrandt et al. ............. 606/46 |
| 4,085,756 | 4/1978 | Weaver ............................. 606/45 |
| 4,381,007 | 4/1983 | Doss . |
| 4,908,011 | 3/1990 | Jabobsen et al. ................ 606/192 |
| 5,006,119 | 4/1991 | Acker et al. ..................... 606/32 |
| 5,057,106 | 10/1991 | Kasevich et al. ................ 606/33 |
| 5,092,348 | 3/1992 | Dubrul et al. .................... 128/899 |
| 5,277,201 | 1/1994 | Stern ................................ 606/32 |

*Primary Examiner*—Jennifer Bahr
*Assistant Examiner*—Michael Peffley
*Attorney, Agent, or Firm*—McAulay Fisher Nissen Goldberg & Kiel, LLP

[57] ABSTRACT

In a method for removing a myoma, an antenna electrode is placed into a patient so that the antenna electrode is in contact with the patient's uterus. A cutting electrode is also inserted into the patient and placed into contact with uterine tissues about a myoma. The antenna electrode and the cutting electrode are energized with radio frequency energy so that the cutting electrode cuts through the uterine tissues.

15 Claims, 1 Drawing Sheet

MYOMA REMOVAL TECHNIQUE AND ASSOCIATED SURGICAL DEVICE

BACKGROUND OF THE INVENTION

This invention relates to a surgical method for removing a myoma from the uterus of a patient. This invention also relates to an associated surgical device for use in performing the method.

A myoma is a fibroid mass of tumorous uterine tissue, solid and benign. A myoma can be as large as a baby's head and can squeeze the Fallopian tubes or the uterine cavity, preventing pregnancy. Because a myoma is massive and incompressible, it poses substantial problems in removal from the abdominal cavity via conventional laparoscopic procedures. Unlike a gall bladder, for example, a myoma frequently cannot be simply pulled through a laparoscopic trocar perforation. Moreover, chopping a myoma into smaller tissue parts can cause a significant amount of bleeding.

One technique is known for the laparoscopic removal of myoma tissues. That technique includes the manual insertion of a tubular member into the myoma, thereby forming a myoma core inside the tubular member. Subsequently, laparoscopic graspers are inserted into the tubular member to pull the myoma tissues therefrom.

This technique is difficult and requires a lot of energy.

A known surgical instrument for dissecting tissues involves the use of radio waves. An antenna electrode in the form of a pad is placed under the patient, while a cutting electrode in the form of a loop is used to do the dissection. During a dissection procedure, the electrodes are energized with radio frequency electromagnetic current.

OBJECT OF THE INVENTION

An object of the present invention is to provide a surgical method for removing myoma tissues.

Another, more specific, object of the present invention is to provide such a method which may be implemented at least partially through laparoscopic procedures.

Another object of the present invention is to provide such a method which is relatively easy and quick.

A further object of the present invention is to provide an associated surgical device for use in removing a myoma.

These and other objects of the present invention will be apparent from the drawings and detailed descriptions herein.

SUMMARY OF THE INVENTION

A method for removing a myoma comprises, in accordance with the present invention, the steps of (a) providing a first cautery instrument with a first electrode at a first distal end and a second cautery instrument with a second electrode at a second distal end, (b) placing the first electrode in contact with tissues of a patient's uterus, (c) positioning the second electrode in contact with myoma tissues of the uterus, and (d) operating the first and the second cautery instrument to cut through the myoma tissues or through uterine tissues proximate to the myoma tissues.

It is contemplated that the first electrode is an antenna electrode and that the electrodes are energized with radio-frequency energy.

According to another feature of the present invention, the antenna electrode is in the form of a balloon. The balloon electrode is inserted in a relatively collapsed configuration through a vagina of the patient and into the patient's uterus and is subsequently inflated.

Alternatively, the antenna electrode may take the form of a cup which is inserted through a laparoscopic trocar sleeve into a peritoneal cavity of the patient and subsequently placed in contact with the patient's uterus and specifically with the myoma which is being removed. In another step of this alternative procedure, where the cup communicates with a vacuum generator, suction is applied to the myoma via the cup to facilitate removal of the myoma from the peritoneal cavity.

In yet another alternative procedure in accordance with the present invention, the electrode takes the form of a screw and is screwed into the myoma tissues.

In any case, the cutting electrode may be inserted into a peritoneal cavity of the patient via a laparoscopic trocar sleeve. In that event, the method further comprises the steps of lifting the patient's abdominal wall and disposing the trocar sleeve in the lifted abdominal wall prior to the step of inserting the cutting electrode into the peritoneal cavity of the patient.

A surgical device comprises, in accordance with the present invention, an electrode in the form of an inflatable balloon, and inflation componentry operatively connected to the balloon for inflating that member. An energization component is operatively connected to the electrode for operating the electrode.

According to another feature of the present invention, the electrode is an antenna electrode, while the energization component includes means for generating in the antenna electrode an electrical current having a radio frequency.

According to a further feature of the present invention, the balloon has a pitted surface for increasing a total effective surface area of the balloon.

The use of a balloon electrode or a cup-shaped web electrode in accordance with the present invention has the advantage of increasing effective power of the surgical assembly, thereby enhancing coagulation, reducing bleeding, and promoting hemostasis.

DETAILED DESCRIPTION

Figure 1:
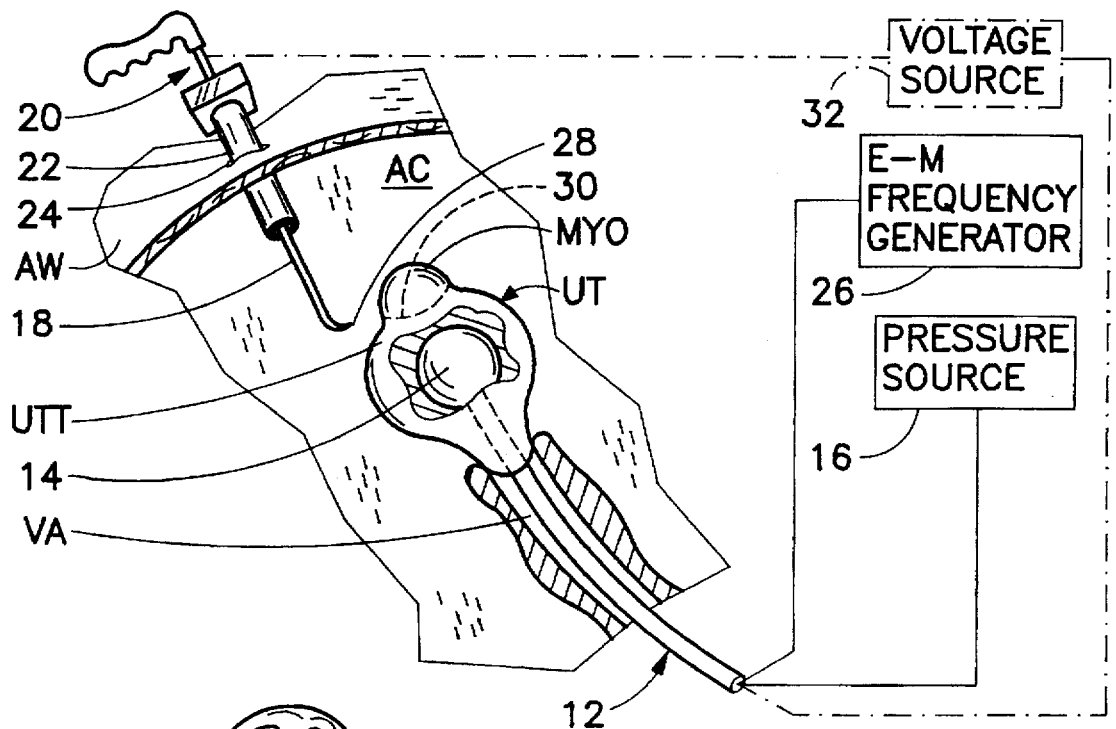
FIG. 1 is partially a block diagram and partially a schematic perspective view of laparoscopic surgical instrumentation, in accordance with the present invention, in use during a surgical procedure, diagrammatically illustrating human organs partially broken away.

As illustrated in FIG. 1, in order to remove a myoma MYO from a patient's uterus UT, a cautery instrument 12, and particularly an inflatable balloon electrode 14 at a distal end of the instrument, is inserted through the vagina VA and into the uterus UT of the patient. Balloon electrode 14 is inserted in a collapsed configuration (not shown) and, upon disposition in uterus UT, is inflated under pressure supplied from a source 16. Source 16 may be any source commonly used in the surgical industry to expand balloons inside patients. Accordingly, source 16 may take the form of a syringe filled with saline solution or, alternatively, a supply of pressurized carbon dioxide gas.

As further illustrated in FIG. 1, a distal end portion 18 of another surgical electrode instrument 20 is inserted into an abdominal or peritoneal cavity AC of the patient through a laparoscopic trocar sleeve 22 which traverses a perforation 24 in an abdominal wall AW of the patient. Abdominal wall AW is lifted, as in other laparoscopic operations, prior to the insertion of instrument 20.

Upon the deployment of instruments 12 and 20, an electromagnetic wave generator 26 operatively connected to instrument 12 is activated to supply an alternating current of radio frequency to balloon electrode 14. To that end, balloon electrode 14 includes an electrically conductive layer (not shown). Balloon electrode 14 may be coated with a nonconductive polymeric film (not shown).

Upon the energization of balloon electrode 14 with radio-frequency current from generator 26, instrument 20 is manipulated from outside the patient to bring a sharp electrode tip 28 into contact with uterine tissues UTT at a boundary 30 between myoma MYO and the body of uterus UT.

During a subsequent severing of myoma MYO from uterus UT, the uterine tissues UTT are cauterized. The severed myoma MYO may be removed from abdominal cavity AC by any known technique. A pouch (not illustrated) with a purse string, for example, may be inserted through a laparoscopic trocar sleeve. Laparoscopic grasping forceps (not shown) may be used to deposit the severed myoma MYO into the pouch. The pouch with the severed myoma is then removed through a trocar sleeve, e.g., sleeve 22, or abdominal perforation 24 after the removal of sleeve 22 from the perforation.

Upon removal of myoma MYO from uterus UT, balloon electrode 14 is deflated and removed from uterus UT via vagina VA.

As additionally illustrated in FIG. 1, instead of radio-frequency cautery, instruments 12 and 20 may be used in a conventional bipolar electrocautery operation. To that end, instruments 12 and 20 are operatively connected to a voltage source 32. In this case, balloon electrode 14 is either not provided with a polymeric coating or else the coating is so thin as to not interfere with the transmission of electrical current from electrode tip 28 to balloon electrode 14.

Figure 2:
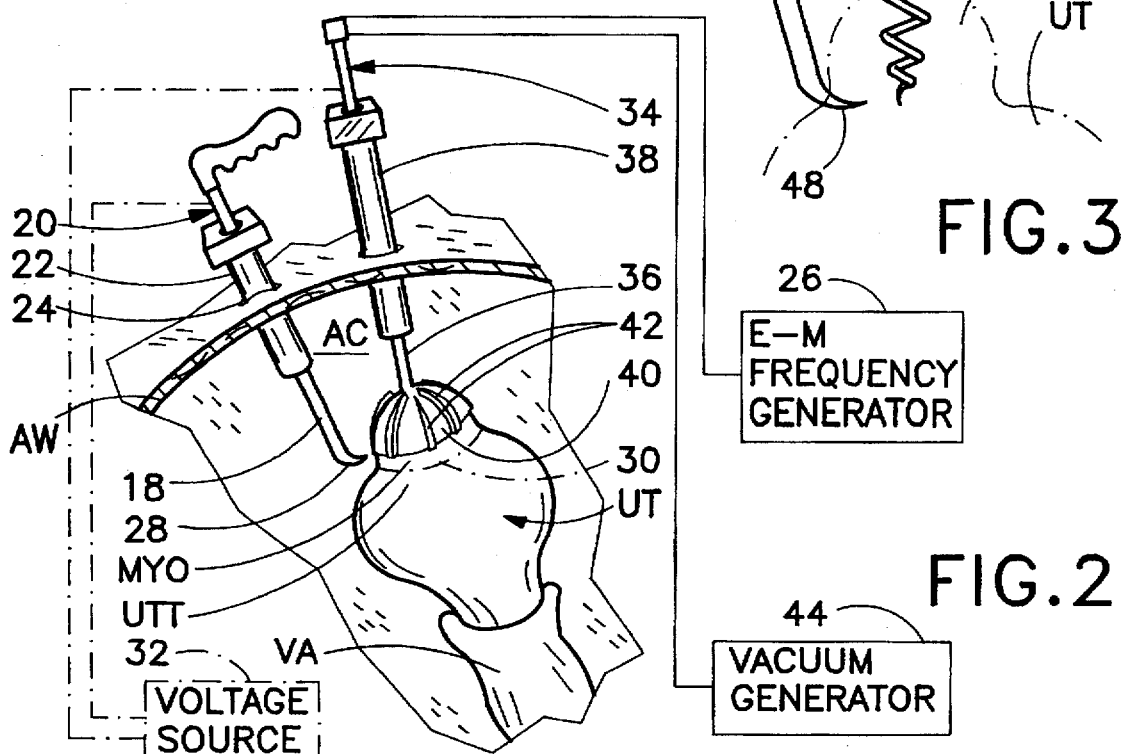
FIG. 2 is partially a block diagram and partially a schematic perspective view similar to FIG. 1, showing modified laparoscopic surgical instrumentation, in accordance with the present invention.

FIG. 2 depicts an alternative electrode assembly for removing a myoma MYO. In FIG. 2, those elements identical to corresponding elements in FIG. 1 have been provided with identical reference designations. The embodiment of FIG. 2 differs from the embodiment of FIG. 1 in that a different first electrode instrument 34 is employed. Electrode instrument 34 is a laparoscopic instrument with a distal end portion 36 inserted through a trocar sleeve 38 into the patient's abdominal or peritoneal cavity AC. At a distal end, instrument 34 is provided with a cup-shaped electrode web 40 which is passed in a collapsed configuration through trocar sleeve 38. Upon emerging from the inner end of trocar sleeve 38, electrode web 40 automatically opens to an expanded configuration (FIG. 2) under the action of spring ribs 42 attached to the web 40 along an outer surface thereof.

As described hereinabove with reference to FIG. 1, electrode web 40 is operatively coupled to electromagnetic (radio frequency) wave generator 26. Upon proper disposition of instruments 20 and 34, generator 26 is activated to supply an alternating current of radio frequency to electrode web 40. Electrode web 40 includes an electrically conductive layer (not shown).

Upon the energization of cup-shaped electrode web 40 with radio-frequency current from generator 26, instrument 20 is manipulated from outside the patient to bring electrode tip 28 into contact with uterine tissues UTT at boundary 30. During a subsequent severing of myoma MYO from uterus UT, the uterine tissues UTT are cauterized. As described above, the severed myoma MYO may be removed from abdominal cavity AC by any known technique. Upon removal of myoma MYO from uterus UT, electrode web 40 is removed from uterus UT via trocar sleeve 38. Upon a pulling of instrument 34 in a proximal direction relative to sleeve 38, ribs 42 are pressed by the distal edge of sleeve 38 to assume a straightened configuration in opposition to their internal spring forces.

As discussed above with reference to FIG. 1, instruments 20 and 34 may be operatively connected to voltage source 32 for implementing a conventional bipolar cautery operation.

As further illustrated in FIG. 2, electrode web 40 may be operatively linked to a vacuum generator 44 for applying suction to myoma MYO to aid in the removal thereof from uterus UT. The vacuum is communicated to a concave inner surface of electrode web 40 via a channel or conduit (not shown) extending along instrument 34.

Figure 3:
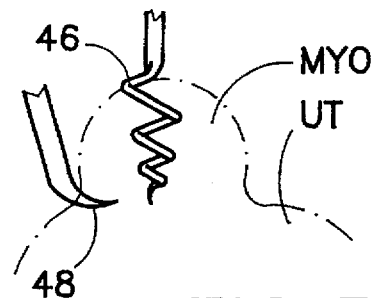
FIG. 3 is a schematic partial side elevational view of further instrumentation in accordance with the present invention for removing a myoma.

As depicted schematically in FIG. 3, a cautery electrode for the removal of a myoma MYO from a uterus UT may take the form of a screw or worm thread 46 which is screwed into myoma MYO. Electrode screw 46 cooperates with a cutting electrode 48 to remove myoma MYO.

Figure 4:
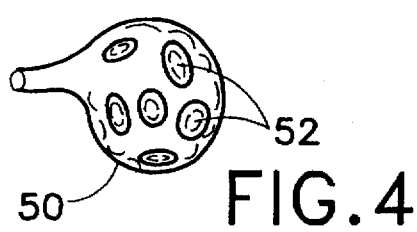
FIG. 4 is a schematic partial side elevational view of a balloon electrode in accordance with the present invention.

As illustrated in FIG. 4, a balloon electrode 50 may be provided with a plurality of indentations or pits 52 for increasing the surface area of the electrode and thus increasing the effective power of the surgical assembly to enhance coagulation, reduce bleeding, and promote hemostasis.

It is to be understood that electrocautery surgical instruments are well known in the medical arts, as demonstrated, for example, by U.S. Pat. No. 4,903,696 to Grabinger et al., U.S. Pat. No. 4,785,807 to Marsden, and U.S. Pat. No. 4,481,948 to Sole, the disclosures of which are hereby incorporated by reference.

Although the invention has been described in terms of particular embodiments and applications, one of ordinary skill in the art, in light of this teaching, can generate additional embodiments and modifications without departing from the spirit of or exceeding the scope of the claimed invention. For example, other equivalent methods for opening electrode web 40 upon an ejection thereof from the distal end of trocar sleeve 38. Screw 46 may take other forms which are equivalent to that illustrated in FIG. 3.

Accordingly, it is to be understood that the drawings and descriptions herein are proffered by way of example to facilitate comprehension of the invention and should not be construed to limit the scope thereof.

What is claimed is:

1. A method for removing a myoma, comprising the steps of:

providing a first dissection and cauterization instrument with a first electrode at a first distal end and a second dissection and cauterization instrument with a second electrode at a second distal end, said first electrode taking the form of a cup;

placing said first electrode in contact with tissues of a patient's uterus, said step of placing including the step of covering a portion of said myoma with said cup;

positioning said second electrode in contact with uterine tissues proximate to a boundary between the myoma and normal tissues of said uterus; and operating said first and said second dissection and cauterization instrument so that said second dissection and cauterization instrument cuts through said uterine tissues proximate to said boundary between said myoma and normal tissues of said uterus.

2. The method defined in claim 1, further comprising the step of applying suction to said myoma via said cup.

3. The method defined in claim 1, further comprising the step of inserting said first dissection and cauterization instrument and said second dissection and cauterization instrument into a peritoneal cavity of the patient via laparoscopic trocar sleeves.

4. A method for removing a myoma, comprising the steps of:

providing an antenna electrode and energization means operatively connected to said electrode for generating in said electrode a current having a radio frequency;

placing said antenna electrode into a patient so that said antenna electrode is in contact with the patient's uterus;

inserting a cutting electrode into the patient;

placing said cutting electrode into contact with uterine tissues about a myoma; and energizing said antenna electrode and said cutting electrode with radio frequency energy so that said cutting electrode cuts through said uterine tissues.

5. The method defined in claim 4 wherein said antenna electrode is in the form of a balloon, said steps of placing said antenna electrode including the steps of inserting said balloon in a relatively collapsed configuration through a vagina of the patient and into the patient's uterus and inflating said balloon upon disposition thereof inside said uterus.

6. The method defined in claim 5, further comprising the step of inserting said cutting electrode into a peritoneal cavity of the patient via a laparoscopic trocar sleeve.

7. The method defined in claim 6, further comprising the steps of lifting the patient's abdominal wall and disposing said trocar sleeve in the lifted abdominal wall prior to said step of inserting said cutting electrode into the peritoneal cavity of the patient.

8. The method defined in claim 4 wherein said antenna electrode takes the form of a cup, said step of placing said antenna electrode including the step of covering a portion of the patient's uterus with said cup.

9. The method defined in claim 8, further comprising the step of applying suction to said myoma tissues via said cup.

10. A method for removing a myoma, comprising the steps of:

providing a first dissection and cauterization instrument with a first electrode at a first distal end and a second dissection and cauterization instrument with a second electrode at a second distal end, said first electrode taking the form of a balloon;

placing said first electrode in contact with tissues of a patient's uterus, said step of placing including the steps of inserting said balloon in a relatively collapsed configuration through a vagina of the patient and into the patient's uterus and inflating said balloon upon disposition thereof inside said uterus;

positioning said second electrode in contact with uterine tissues proximate to a boundary between the myoma and normal tissues of said uterus; and operating said first and said second dissection and cauterization instrument so that said second dissection and cauterization instrument cuts through said uterine tissues proximate to said boundary between said myoma and normal tissues of said uterus.

11. The method defined in claim 10, further comprising the step of inserting said second dissection and cauterization instrument into a peritoneal cavity of the patient via a laparoscopic trocar sleeve.

12. The method defined in claim 11, further comprising the steps of lifting the patient's abdominal wall and disposing said trocar sleeve in the lifted abdominal wall prior to said step of inserting.

13. The method defined in claim 7 wherein said first electrode is an antenna electrode, said step of operating including the step of generating radio-frequency current in one of said first electrode and said second electrode.

14. A method for removing a myoma, comprising the steps of:

providing a first dissection and cauterization instrument with a first electrode at a first distal end and a second dissection and cauterization instrument with a second electrode at a second distal end, said first electrode taking the form of a screw;

placing said first electrode in contact with tissues of a patient's uterus, said step of placing including the step of inserting said screw into said myoma;

positioning said second electrode in contact with uterine tissues proximate to a boundary between the myoma and normal tissues of said uterus; and operating said first and said second dissection and cauterization instrument so that said second dissection and cauterization instrument cuts through said uterine tissues proximate to said boundary between said myoma and normal tissues of said uterus.

15. The method defined in claim 14, further comprising the step of inserting said first dissection and cauterization instrument and said second dissection and cauterization instrument into a peritoneal cavity of the patient via laparoscopic trocar sleeves.

* * * * *